(12) United States Patent
Kannan et al.

(10) Patent No.: US 9,308,258 B2
(45) Date of Patent: Apr. 12, 2016

(54) STABLE AND AGGREGATION FREE ANTIBODY FC MOLECULES THROUGH CH3 DOMAIN INTERFACE ENGINEERING

(75) Inventors: Gunasekaran Kannan, Westlake Village, CA (US); Hongxing Zhou, Bellevue, WA (US)

(73) Assignee: Amgen Inc., Thousand Oaks, CA (US)

( * ) Notice: Subject to any disclaimer, the term of this patent is extended or adjusted under 35 U.S.C. 154(b) by 312 days.

(21) Appl. No.: 13/382,876

(22) PCT Filed: Jun. 29, 2010

(86) PCT No.: PCT/US2010/040471
§ 371 (c)(1),
(2), (4) Date: Jan. 6, 2012

(87) PCT Pub. No.: WO2011/005621
PCT Pub. Date: Jan. 13, 2011

(65) Prior Publication Data
US 2012/0116057 A1    May 10, 2012

Related U.S. Application Data

(60) Provisional application No. 61/223,831, filed on Jul. 8, 2009.

(51) Int. Cl.
*C12N 15/13* (2006.01)
*C12N 15/63* (2006.01)
*A61K 39/395* (2006.01)

(52) U.S. Cl.
CPC ....... *A61K 39/39591* (2013.01); *C07K 2317/52* (2013.01)

(58) Field of Classification Search
CPC .............................. C12N 15/13; C12N 15/63
USPC .......... 530/387.3, 389.1; 536/23.53; 435/326, 435/320.1, 69.6, 252.33
See application file for complete search history.

(56) References Cited

U.S. PATENT DOCUMENTS

| 2006/0074225 | A1 | 4/2006 | Chamberlain et al. |
| 2010/0286374 | A1 | 11/2010 | Kannan et al. |
| 2013/0245233 | A1* | 9/2013 | Lei et al. .................... 530/387.3 |

FOREIGN PATENT DOCUMENTS

| WO | 2007/022070 A2 | 2/2007 |
| WO | 2007/110205 | 10/2007 |
| WO | 2007/124077 A2 | 11/2007 |
| WO | 2010/063785 | 6/2010 |
| WO | 2013097430 | * 7/2013 |

OTHER PUBLICATIONS

Julie Burke (Biotechnology Chemical Pharmaceutical Customer Partnership meeting in March of 2009; p. 1; Mar. 2009).*
Kannan et al. J. Biol. Chem. 285:19637-19646 (2010).*
Salfeld (Nature Biotech. 25(12): 1369-1372 (2007)).*
Dall'Acqua (J. Immunol. 177:1129-1138 (2006)).*
Dufner (Trends Biotechnol. 24(11):523-29 (2006)).*
Dall'Acqua et al., "Contribution of domain interface residues to the stability of antibody CH3 domain homodimers," Biochemistry 37:9266-9273, 1998.
Bogan and Thorn, "Anatomy of hot spots in protein interfaces," J Mol Biol 280:1-9, 1998.
Gabdoulline and Wade, "Biomolecular diffusional association," Curr Opin Struct Biol 12:204-213, 2002.
Halperin et al., "Protein-protein interactions: coupling of structurally conserved residues and of hot spots across interfaces. Implications for docking," Structure 12:1027-1038, 2004.
Joachimiak et al., "Computational design of a new hydrogen bond network and at least a 300-fold specificity switch at a protein-protein interface," J Mol Biol 361:195-208, 2006.
Kortemme and Baker, "Computational design of protein-protein interactions," Curr Opin Chem Biol 8:91-97, 2004/.
Kortemme et al., "Computational redesign of protein-protein interaction specificity," Nat Struct Biol 11:371-379, 2004.
Marvin and Lowman, "Redesigning an antibody fragment for faster association with its antigen," Biochemistry 42:7077-7083, 2003.
Nohaile et al., "Altering dimerization specificity by changes in surface electrostatics," Proc Natl Acad Sci USA 98(6):3109-3114, 2001.
Ridgway et al., "'Knobs-into-holes' engineering of antibody $C_H3$ domains for heavy chain heterodimerization," Protein Eng Des Sel 9(7):617-621, 1996.
Schreiber, "Electrostatic design of protein-protein association rates," Methods Mol Biol 340:235-249, 2006.
Selzer et al., "Rational design of faster associating and tighter binding protein complexes," Nat Struct Biol 7:537-541, 2000.
Sheinerman et al., "Electrostatic aspects of protein-protein interactions," Curr Opin Struct Biol 10:153-159, 2000.
Sinha and Smith-Gill, "Electrostatics in protein binding and function," Curr Protein Pept Sci 3: 601-614, 2002.
Szczepek et al., Structure-based redesign of the dimerization interface reduces the toxicity of zinc-finger nucleases, Nat Biotechnol 25:786-793, 2007.
Zhu et al., "Remodeling domain interfaces to enhance heterodimer formation," Protein Sci 6:781-788, 1997.

* cited by examiner

*Primary Examiner* — Lynn Bristol
(74) *Attorney, Agent, or Firm* — Nathan A. Machin

(57) ABSTRACT

The present invention relates to methods of increasing stability and reducing aggregation in compositions comprising antibody Fc molecules and to composition comprising such molecules. Certain amino acid substitutions in the CH3 domain result in increased stability and reduced aggregation of compositions containing polypeptides comprising a CH3 domain, e.g., an antibody or Fc-fusion protein.

17 Claims, 5 Drawing Sheets

HMSSVSAQAAAEPKSSDKTHTCPPCPAPELLGGPSVFLFPPKPKDTLMISRTPEVT
CVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQG
NVFSCSVMHEALHNHYTQKSLSLSPGK

FIG. 2

| Fc-Type | Property | TM1 | TM2 |
|---|---|---|---|
| WT S364S | Cpmax (°C) | 71.1 | 81.8 |
| | ΔH (kcal/mol) | 41.4 | 66.5 |
| Mut S364T | Cpmax (°C) | 71.2 | 78.4 |
| | ΔH (kcal/mol) | 45.4 | 48.8 |
| Mut S364A | Cpmax (°C) | 69.0 | 70.8 |
| | ΔH (kcal/mol) | 62.32 | 72.1 |
| Fc-S364V | Cpmax (°C) | 67.40 | 69.13 |
| | ΔH (kcal/mol) | 65.1 | 55.9 |

STABLE AND AGGREGATION FREE ANTIBODY FC MOLECULES THROUGH CH3 DOMAIN INTERFACE ENGINEERING

CROSS-REFERENCE TO RELATED APPLICATIONS

This application is a National Stage application under 35 U.S.C. §371 of International Application No. PCT/US2010/040471 (which designated the United States), having an international filing date of Jun. 29, 2010, which claims the benefit of U.S. provisional patent application No. 61/223,831, filed Jul. 8, 2009, which is hereby incorporated by reference.

REFERENCE TO THE SEQUENCE LISTING

The present application is being filed along with a Sequence Listing in electronic format. The Sequence Listing is provided as a file entitled A-1434-US-PCT_Seq_Listing_ST25.txt, created Dec. 20, 2011, which is 15 KB in size. The information in the electronic format of the Sequence Listing is incorporated herein by reference in its entirety.

BACKGROUND OF THE INVENTION

Antibodies have become the modality of choice within the biopharma industry because they possess several characteristics that are attractive to those developing therapeutic molecules. Along with the ability to target specific structures or cells, antibodies make its target susceptible to Fc-receptor cell-mediated phagocytosis and killing (Raghavan and Bjorkman 1996). Further, the antibody's ability to interact with neonatal Fc-receptor (FcRn) in a pH dependent manner confers it with extended serum half-life (Ghetie and Ward 2000). This unique feature of antibodies allows extending the half-life of therapeutic protein or peptide in the serum by engineering Fc-fusion molecules.

Antibodies belong to the immunoglobulin class of proteins which includes IgG, IgA, IgE, IgM, and IgD. The most abundant immunoglobulin class in human serum is IgG (Deisenhofer 1981; Huber 1984; Roux 1999). The IgG structure has four chains, two light and two heavy chains; each light chain has two domains and each heavy chain has four domains. The antigen binding site is located in the Fab region (Fragment antigen binding) which contains a variable light (VL) and a variable heavy (VH) chain domain as well as constant light (LC) and constant heavy (CH1) chain domains. The CH2 and CH3 domain region of the heavy chain is called Fc (Fragment crystallizable). The IgG molecule can be considered as a heterotetramer having two heavy chains that are held together by disulfide bonds (—S—S—) at the hinge region and two light chains. The number of hinge disulfide bonds varies among the immunoglobulin subclasses (Papadea and Check 1989). The FcRn binding site is located in the Fc region of the antibody (Martin, West et al. 2001), and thus the extended serum half-life property of the antibody is retained in the Fc fragment. The Fc region alone can be thought of as a homodimer of heavy chains comprising CH2 and CH3 domains.

Because antibodies and other Fc containing molecules are complex molecules, commercial production of such molecules can be complicated by heterogeneity in the final product. This heterogeneity can lead to decreased stability due to degradation and aggregation of the end product, which leads to a decrease in yield. To increase stability of the Fc-containing therapeutic drug products, companies go to great lengths to optimize production processes and drug formulations. Given the cost of producing these molecules, even minor changes in yield can lead to great cost savings.

SUMMARY OF THE INVENTION

This invention provides improved homogeneity of purified IgG1 and IgG1 Fc-fusion molecules. It is often noted in the purified IgG1 and/or Fc fusion molecules that there is significant amount of aggregation. For example, based on SEC analysis, the wild type (WT) Fc molecule described in the Examples demonstrated aggregation up to 18%. The invention described herein demonstrates that by altering the CH3 domain interface, it is possible to reduce the level of aggregation in the final purified material.

Thus, embodiments of the invention include Fc-containing polypeptides and proteins comprising an altered CH3 domain wherein the alteration increases stability of the purified polypeptide or protein as compared to when comprising wild-type CH3 domain. In polypeptides or proteins comprising an IgG CH3 domain, substitution of Ser364 leads to decreased aggregation. The preferred substitution is to alanine. The Fc-containing polypeptides include, but are not limited to, antibodies and Fc-fusion molecules.

The proteins and polypeptides of the invention are particularly useful in pharmaceutical compositions. Such compositions contain low levels of aggregation. For example, the pharmaceutical compositions of the invention can comprise less than 10%, less than 5%, less than 2%, or even less than 1% aggregation of the CH3 domain-containing molecule. Aggregation can be measured by a number of techniques, including size exclusion chromatography.

Also provided herein are methods of reducing aggregation of a polypeptide or protein comprising a CH3 domain. Such methods include mutating a nucleic acid to substitute serine at position 364 with another amino acid, expressing the nucleic acid in a recombinant host cell to produce a polypeptide comprising a CH3 domain having an amino acid substitution at Ser364, and purifying the polypeptide from the culture. In preferred embodiments the purified polypeptide is formulated into a pharmaceutical composition having less than less than 10%, less than 5%, less than 2%, or even less than 1% aggregation of the of the polypeptide or protein comprising a wild-type CH3 domain.

BRIEF DESCRIPTION OF THE DRAWINGS

FIG. 2 is the wild type human IgG1 Fc sequence (SEQ ID NO:1) used in the Examples. S364 position is highlighted in the sequence.

DETAILED DESCRIPTION

Figure 1A:
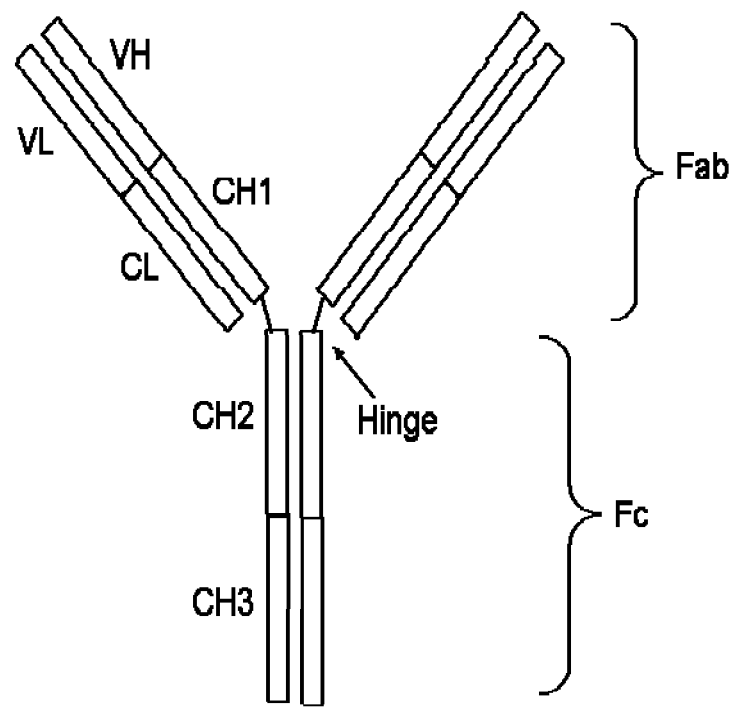
FIG. 1A is a schematic structure of an IgG1.
Figure 1B:
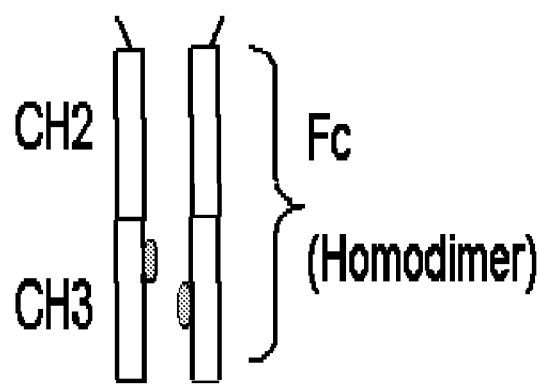
FIG. 1B is an Fc Homodimer with S364 position shown in light shading. This construct was used as a control.
Figure 1C:
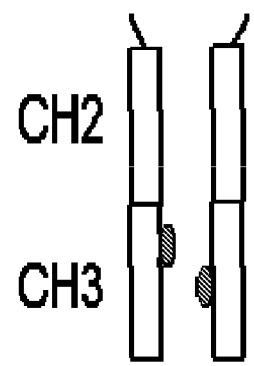
FIG. 1C depicts a S364A mutant shown in dark shading.

Alterations in amino acids comprising the antibody CH3-CH3 interface can lead to greater stability and reduced aggregation of purified CH3-containing molecules. The amino acids making up the CH3-CH3 interface are described in co-owned provisional applications 61/019,569, filed Jan. 7, 2008, and 61/120,305, filed Dec. 5, 2009, along with PCT/US2009/000071, filed Jan. 6, 2009 (all incorporated by reference in their entirety). In particular, CH3-containing molecules comprising a substitution in the amino acid corresponding to Ser364 display greater stability and less aggregation than those containing wild-type CH3.

As used herein, "Ser364" refers to the amino acid at position 364 in the IgG antibody heavy chain based on the EU numbering scheme of Kabat. In FIG. 2, an exemplary IgG1 Fc wild-type sequence is shown having the amino acid corresponding to Ser364 underlined. By "wild-type sequence," it is meant a sequence of amino acids that occurs naturally within a species of animals, e.g., humans. Wild-type sequence may vary slightly between individuals within a population, e.g., different alleles for the various immunoglobulin chains are known in the art.

The compositions and methods of the present invention are not limited to the exemplary alleles disclosed herein but include those having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, and at least 99% identity to an exemplary allele disclosed herein. For purposes of comparison of the characteristics of the CH3-containing molecules of the present invention to those of wild-type human CH3-containing molecules, the wild-type sequences are those set forth in SEQ ID NOS:2-5 (IgG1, IgG2, IgG3, and IgG4, respectively).

In certain embodiments of the invention, Ser 364 is substituted with alanine (Ser364A). Exemplary Ser364A CH3 domains for human IgG1, IgG2, IgG3, and IgG4 are set forth in SEQ ID NOS:6-9, respectively. In other embodiments, Ser 364 is substituted with valine (Ser364V). Exemplary Ser364V CH3 domains for human IgG1, IgG2, IgG3, and IgG4 are set forth in SEQ ID NOS:10-13, respectively.

It is contemplated that the stability and aggregation benefits of the IgG Ser364 variants are not limited to IgG but are also applicable to other immunoglobulin subclasses including IgA, IgE, IgD, and IgM.

Virtually any molecule that contains a CH3 domain may comprise a CH3 domain of the present invention. In certain embodiments, a CH3-containing polypeptide is an antibody, a bispecific antibody, a monospecific antibody, a bispecific maxibody, a monobody, a peptibody, a bispecific peptibody, a monovalent peptibody, and an Fc-fusion protein, e.g., a receptor fusion protein.

The Ser364-substituted polypeptides of the present invention demonstrate reduced aggregation as compared to the identical polypeptide comprising Ser364. Thus, embodiments of the invention include compositions comprising an antibody or Fc-fusion molecule wherein the amount of aggregation of said antibody or Fc-fusion molecule is less than 15%, less than 14%, less than 13%, less than 12%, less than 11%, less than 10%, less than 9%, less than 8%, less than 7%, less than 6%, less than 5%, less than 4%, less than 3%, less than 2%, or less than 1%. Aggregation may be measured by a number of techniques known in the arts. Preferred methods of measuring aggregation include the use of size exclusion chromatography.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings: The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular polypeptide or polynucleotide sequence also can be described by explaining how it differs from a reference sequence.

The terms "peptide" "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150, 200, 250, 300, 350, or 400 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein or an artificial amino acid sequence.

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

A "variant" of a polypeptide comprises an amino acid sequence wherein one or more amino acid residues are inserted into, deleted from and/or substituted into the amino acid sequence relative to another polypeptide sequence. Variants of the invention include those comprising variant CH2 or CH3 domains. In certain embodiments, in addition to a substitution at Ser364, a variant comprises one or more mutations that when present in an Fc molecule increase affinity for the polypeptide to one or more FcγRs. Such variants demonstrate enhanced antibody-dependent cell-mediated cytotoxicity. Examples of variants providing such are described in U.S. Pat. No. 7,317,091.

Other variants include those that decrease the ability of CH3-domain containing polypeptides to homodimerize, while increasing the ability to heterodimerize. Examples of such Fc variants are described in U.S. Pat. Nos. 5,731,168 and 7,183,076. Further examples are described in the co-owned U.S. Provisional Applications 61/019,569, filed Jan. 7, 2008, and 61/120,305, filed Dec. 5, 2008 (both incorporated by reference in their entirety).

A "derivative" of a polypeptide is a polypeptide (e.g., an antibody) that has been chemically modified, e.g., via conjugation to another chemical moiety such as, for example, polyethylene glycol, a cytotoxic agent, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described herein.

The CH3 domain-containing polypeptide can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5th Ed., US Dept. of Health and Human Services, PHS, NIH, NIH Publication no. 91-3242, 1991. Intact antibodies include polyclonal, monoclonal, chimeric, humanized or fully human having full length heavy and light chains.

An antibody may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes. One or more genes encoding the human heavy chains may be altered to contain a Ser362 mutation. When such mice are immunized with an antigen, the mice will produce human antibodies having a Ser364 mutation.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., 1991, Science 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody"

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody or an Fc-fusion, and a derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Exemplary host cells include Chinese hamster ovary (CHO) cell lines or their derivatives including CHO strain DXB-11, which is deficient in DHFR (see Urlaub et al., 1980, Proc. Natl. Acad. Sci. USA 77:4216-20), CHO cell lines which grow in serum-free media (see Rasmussen et al., 1998, Cytotechnology 28:31), CS-9 cells, a derivative of DXB-11 CHO cells, and AM-1/D cells (described in U.S. Pat. No. 6,210,924). Other CHO cells lines include CHO-K1 (ATCC #CCL-61), EM9 (ATCC #CRL-1861), and UV20 (ATCC #CRL-1862). Examples of other host cells include COS-7 line of monkey kidney cells (ATCC CRL 1651) (see Gluzman et al., 1981, Cell 23:175), L cells, C127 cells, 3T3 cells (ATCC CCL 163), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell.

The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Pharmaceutical Compositions

The improved stability and reduced aggregation characteristics of the polypeptides of the invention renders them particularly useful for formulation into pharmaceutical compositions. Such compositions comprise one or more additional components such as a physiologically acceptable carrier, excipient or diluent. Optionally, the composition additionally comprises one or more physiologically active agents, for example, as described below. In various particular embodiments, the composition comprises one, two, three, four, five, or six physiologically active agents in addition to one or more antibody and/or Fc-fusion protein of the present invention.

In one embodiment, the pharmaceutical composition comprises an antibody and/or Fc-fusion protein of the invention together with one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in Remington's Pharmaceutical Sciences, 16th Ed. (1980) and 20th Ed. (2000), Mack Publishing Company, Easton, Pa.

Kits for use by medical practitioners are provided including one or more antibody and/or Fc-fusion proteins of the invention and a label or other instructions for use in treating any of the conditions discussed herein. In one embodiment, the kit includes a sterile preparation of one or more antibody and/or Fc-fusion protein, which may be in the form of a composition as disclosed above, and may be in one or more vials.

Dosages and the frequency of administration may vary according to such factors as the route of administration, the particular antibody and/or Fc-fusion protein employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

An antibody and/or Fc-fusion protein of the invention may be administered, for example, once or more than once, e.g., at regular intervals over a period of time. In particular embodiments, an antibody and/or Fc-fusion protein is administered over a period of at least once a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the antibody and/or Fc-fusion protein is administered until the patient manifests a medically relevant degree of improvement over baseline for the chosen indicator or indicators.

As is understood in the pertinent field, pharmaceutical compositions comprising the antibody and/or Fc-fusion protein of the invention are administered to a subject in a manner appropriate to the indication. Pharmaceutical compositions may be administered by any suitable technique, including but not limited to parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antibody and/or Fc-fusion protein in aerosol form, and the like. Other alternatives include oral preparations including pills, syrups, or lozenges.

EXAMPLES

The CH3 domain contains 24 domain interface residues. The change in free energy due to alanine mutation of each interface residue was determined (Table 1). Most mutants resulted in an estimated positive change in free energy as compared to WT and thus were predicted to have a destabilizing effect. Mutation of some residues resulted in an estimated negative change is free energy as compared to WT. Of these, S364A had the greatest estimated change in energy (>1 kcal/mol).

IgG1 Fc variants were created by mutating the codon for Ser364 in IgG1 Fc to that of 18 other amino acids (Ser and Cys excluded) using QuikChange site-directed mutagenesis (Strategene). Expected mutations were confirmed by DNA sequencing. The wild type and mutant Fc proteins were expressed in 293E cell using a pTT5 transient mammalian expression vector (Durocher Y., Perret S., and Kamen A., Nucleic Acid Research 30(2):E9). The Fc proteins were purified using standard protein A chromatography (5 ml column, Pierce).

TABLE 1

Estimation of change in free energy due to alanine mutation for the 24 CH3 domain interface residues.

| Protein Mutation | Energy in Complexed | Energy in uncomplexed | Uncomplexed − Complexed | Change in Energy due to Mutation |
|---|---|---|---|---|
| WT | −3213.6 | −2905.56 | −308.039 | 0.0000 |
| Q347A | −3187.03 | −2883.37 | −303.658 | 0.4381 |
| Y349A | −3141.55 | −2868.98 | −272.572 | 3.5467 |
| T350A | −3170.78 | −2863.86 | −306.918 | 0.1121 |
| L351A | −3164 | −2881.58 | −282.419 | 2.5620 |
| S354A | −3197.35 | −2886.95 | −310.398 | −0.2359 |

TABLE 1-continued

Estimation of change in free energy due to alanine mutation for the 24 CH3 domain interface residues.

| Protein Mutation | Energy in Complexed | Energy in uncomplexed | Uncomplexed − Complexed | Change in Energy due to Mutation |
|---|---|---|---|---|
| R355A | −2972.29 | −2664.13 | −308.159 | −0.0120 |
| D356A | −3134.09 | −2830.67 | −303.417 | 0.4622 |
| E357A | −3156.4 | −2860.77 | −295.63 | 1.2409 |
| K360A | −3184.88 | −2882.18 | −302.7 | 0.5339 |
| S364A | −3208.32 | −2882.76 | −325.564 | −1.7525 |
| T366A | −3189.15 | −2885.05 | −304.104 | 0.3935 |
| L368A | −3157.96 | −2868.36 | −289.604 | 1.8435 |
| K370A | −3161.52 | −2865.56 | −295.959 | 1.2080 |
| N390A | −3155.92 | −2847.78 | −308.144 | −0.0105 |
| K392A | −3173.99 | −2891.42 | −282.572 | 2.5467 |
| T394A | −3177.1 | −2879.89 | −297.204 | 1.0835 |
| P395A | −3201.19 | −2901.89 | −299.3 | 0.8739 |
| V397A | −3186.29 | −2890.18 | −295.94 | 1.2099 |
| D399A | −3125.02 | −2829.92 | −295.093 | 1.2946 |
| S400A | −3198.81 | −2890.01 | −308.799 | −0.0760 |
| F405A | −3131.7 | −2861.56 | −270.139 | 3.7900 |
| Y407A | −3136.62 | −2868.42 | −268.204 | 3.9835 |
| K409A | −3174.99 | −2879.04 | −295.956 | 1.2083 |
| K439A | −3184.85 | −2882.19 | −302.657 | 0.5382 |

Figure 3:
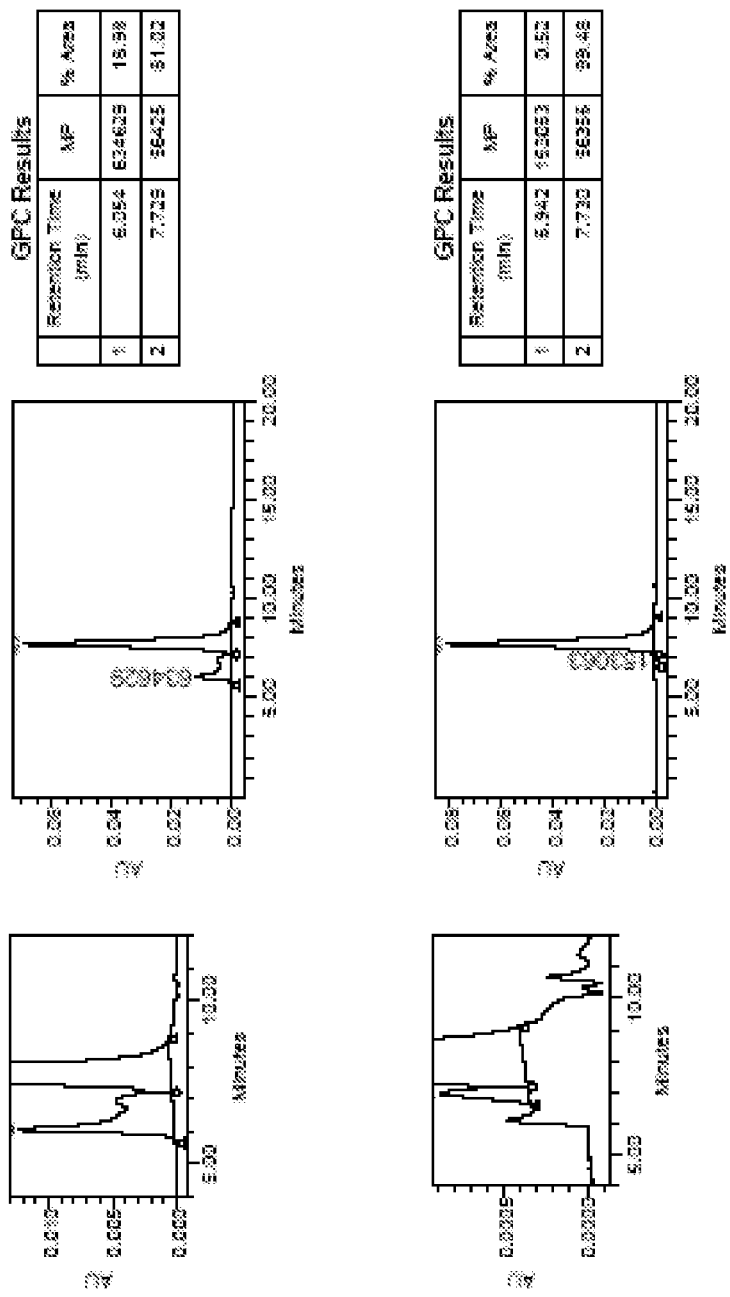
FIG. 3 is the SEC profile showing the monomeric nature of the Fc S364A mutant. The Fc WT has nearly 19% higher order soluble aggregates, whereas Fc S364A mutant has less than 1% aggregation.
Figure 4:
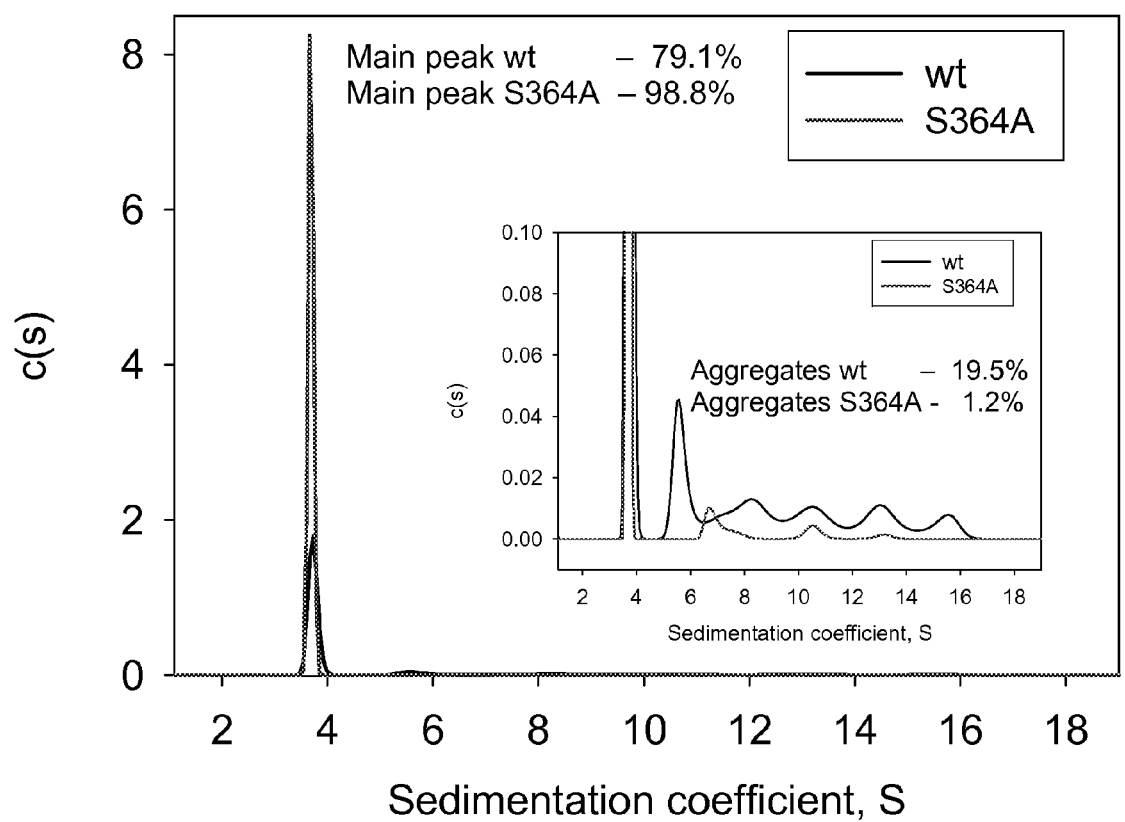
FIG. 4 depicts confirmation of monomeric nature of the Fc WT using AUC. The aggregates estimations are in agreement with SEC analysis. Though slightly higher concentration (0.60 mg/ml) of Fc S364A mutant was used compared to the Fc WT (0.4 mg/ml) in the experiment, the mutant has less than 1% aggregation. This experiment was also repeated with equal concentration of mutant and Fc WT and the estimation of the aggregates was the same.
Figure 5:
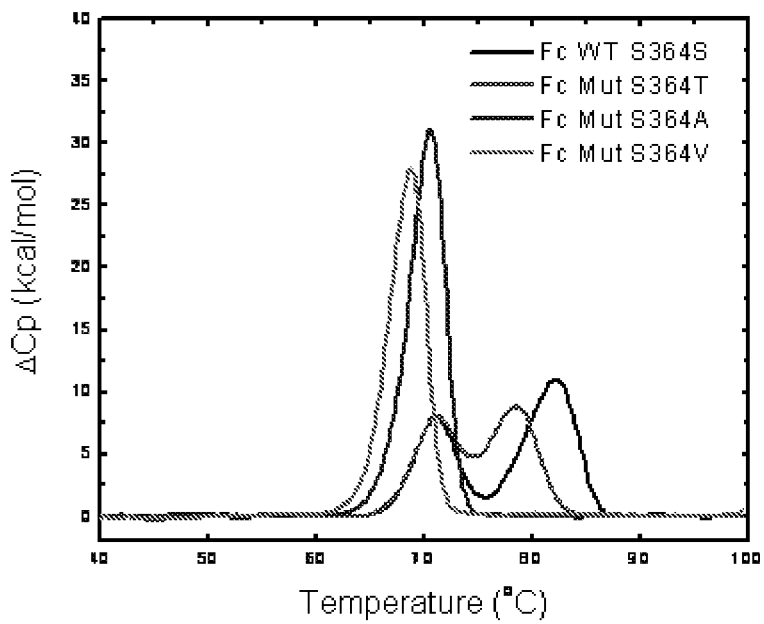
FIG. 5 depicts the differential scanning calorimetry experiment on the Fc WT and selected Fc S364 mutants. The S364A mutant had 15% higher enthalpy than the Fc WT as well as single transition in the DSC suggesting that the CH2 and CH3 domain unfolds cooperatively.

The mutants were analyzed through Size Exclusion Chromatography (SEC), Differential Scanning calorimetry (DSC) experiments, and Analytical Ultra Centrifugation (AUC). The Ser364A mutant had higher enthalpy as well as complete monomeric Fc SEC/AUC profile without higher order aggregates. See FIGS. 3-5

Fc protein homogeneity analysis (SEC) was performed using a TOSO46 mm SW3000 column (TOSO Biosciences LLC, PA).

What is claimed:

1. A polypeptide homodimer comprising an IgG CH3 domain homodimer, wherein said CH3 domain comprises the amino acid sequence set forth in SEQ ID NO:2, SEQ ID NO:3, SEQ ID NO:4, or SEQ ID NO:5 comprising an alanine substitution at Ser364.

2. The polypeptide homodimer of claim 1, wherein the polypeptide comprises a IgG CH2 and CH3 domain.

3. The polypeptide homodimer of claim 2, wherein the polypeptide comprises a IgG heavy chain.

4. An isolated antibody comprising the polypeptide of claim 1.

5. An isolated Fc-fusion protein comprising the polypeptide of claim 1.

6. A pharmaceutical composition comprising the polypeptide homodimer of claim 1.

7. A pharmaceutical composition comprising the isolated antibody of claim 4.

8. A pharmaceutical composition comprising the isolated Fc-fusion protein of claim 5.

9. An isolated nucleic acid comprising a nucleotide sequence encoding the polypeptide of claim 1.

10. An isolated expression vector comprising a nucleotide sequence encoding the polypeptide of claim 1 operably linked to a promoter.

11. An isolated host cell comprising the expression vector of claim 10.

12. The host cell of claim 11, wherein the cell is a prokaryote.

13. The host cell of claim 12, wherein the prokaryote is *E. coli*.

14. The host cell of claim 11, wherein the cell is a mammalian cell line.

15. The host cell of claim 14, wherein the mammalian cell line is a Chinese hamster ovary cell line.

16. A method of reducing aggregation of a polypeptide comprising a CH3 domain having a serine at position 364, said method comprising:
   a) mutating a nucleic acid encoding the polypeptide such that the serine at position 364 is substituted with alanine;

b) expressing the nucleic acid of a) in a recombinant host cell culture to produce a polypeptide comprising a CH3 domain having an alanine substitution at Ser364;

c) purifying the polypeptide from the culture, wherein aggregation of the purified polypeptide is less than 10%.

17. The method of claim 16, further comprising formulating the purified polypeptide into a pharmaceutical composition.

* * * * *

SEQUENCE LISTING

```
<160> NUMBER OF SEQ ID NOS: 13

<210> SEQ ID NO 1
<211> LENGTH: 243
<212> TYPE: PRT
<213> ORGANISM: Homo sapiens

<400> SEQUENCE: 1

His Met Ser Ser Val Ser Ala Gln Ala Ala Glu Pro Lys Ser Ser
1               5                   10                  15

Asp Lys Thr His Thr Cys Pro Pro Cys Pro Ala Pro Glu Leu Leu Gly
                20                  25                  30

Gly Pro Ser Val Phe Leu Phe Pro Pro Lys Pro Lys Asp Thr Leu Met
            35                  40                  45

Ile Ser Arg Thr Pro Glu Val Thr Cys Val Val Val Asp Val Ser His
    50                  55                  60

Glu Asp Pro Glu Val Lys Phe Asn Trp Tyr Val Asp Gly Val Glu Val
65                  70                  75                  80

His Asn Ala Lys Thr Lys Pro Arg Glu Glu Gln Tyr Asn Ser Thr Tyr
                85                  90                  95

Arg Val Val Ser Val Leu Thr Val Leu His Gln Asp Trp Leu Asn Gly
            100                 105                 110

Lys Glu Tyr Lys Cys Lys Val Ser Asn Lys Ala Leu Pro Ala Pro Ile
        115                 120                 125

Glu Lys Thr Ile Ser Lys Ala Lys Gly Gln Pro Arg Glu Pro Gln Val
    130                 135                 140

Tyr Thr Leu Pro Pro Ser Arg Glu Glu Met Thr Lys Asn Gln Val Ser
145                 150                 155                 160

Leu Thr Cys Leu Val Lys Gly Phe Tyr Pro Ser Asp Ile Ala Val Glu
                165                 170                 175

Trp Glu Ser Asn Gly Gln Pro Glu Asn Asn Tyr Lys Thr Thr Pro Pro
            180                 185                 190

Val Leu Asp Ser Asp Gly Ser Phe Phe Leu Tyr Ser Lys Leu Thr Val
        195                 200                 205

Asp Lys Ser Arg Trp Gln Gln Gly Asn Val Phe Ser Cys Ser Val Met
    210                 215                 220
```

```
His Glu Ala Leu His Asn His Tyr Thr Gln Lys Ser Leu Ser Leu Ser
225                 230                 235                 240

Pro Gly Lys

<210> SEQ ID NO 2
<211> LENGTH: 109
<212> TYPE: PRT
<213> ORGANISM: Homo sapiens

<400> SEQUENCE: 2

Ala Lys Gly Gln Pro Arg Glu Pro Gln Val Tyr Thr Leu Pro Pro Ser
1               5                   10                  15

Arg Glu Glu Met Thr Lys Asn Gln Val Ser Leu Thr Cys Leu Val Lys
            20                  25                  30

Gly Phe Tyr Pro Ser Asp Ile Ala Val Glu Trp Glu Ser Asn Gly Gln
        35                  40                  45

Pro Glu Asn Asn Tyr Lys Thr Thr Pro Pro Val Leu Asp Ser Asp Gly
    50                  55                  60

Ser Phe Phe Leu Tyr Ser Lys Leu Thr Val Asp Lys Ser Arg Trp Gln
65                  70                  75                  80

Gln Gly Asn Val Phe Ser Cys Ser Val Met His Glu Ala Leu His Asn
                85                  90                  95

His Tyr Thr Gln Lys Ser Leu Ser Leu Ser Pro Gly Lys
            100                 105

<210> SEQ ID NO 3
<211> LENGTH: 109
<212> TYPE: PRT
<213> ORGANISM: Homo sapiens

<400> SEQUENCE: 3

Thr Lys Gly Gln Pro Arg Glu Pro Gln Val Tyr Thr Leu Pro Pro Ser
1               5                   10                  15

Arg Glu Glu Met Thr Lys Asn Gln Val Ser Leu Thr Cys Leu Val Lys
            20                  25                  30

Gly Phe Tyr Pro Ser Asp Ile Ala Val Glu Trp Glu Ser Asn Gly Gln
        35                  40                  45

Pro Glu Asn Asn Tyr Lys Thr Thr Pro Pro Met Leu Asp Ser Asp Gly
    50                  55                  60

Ser Phe Phe Leu Tyr Ser Lys Leu Thr Val Asp Lys Ser Arg Trp Gln
65                  70                  75                  80

Gln Gly Asn Val Phe Ser Cys Ser Val Met His Glu Ala Leu His Asn
                85                  90                  95

His Tyr Thr Gln Lys Ser Leu Ser Leu Ser Pro Gly Lys
            100                 105

<210> SEQ ID NO 4
<211> LENGTH: 109
<212> TYPE: PRT
<213> ORGANISM: Homo sapiens

<400> SEQUENCE: 4

Thr Lys Gly Gln Pro Arg Glu Pro Gln Val Tyr Thr Leu Pro Pro Ser
1               5                   10                  15

Arg Glu Glu Met Thr Lys Asn Gln Val Ser Leu Thr Cys Leu Val Lys
            20                  25                  30

Gly Phe Tyr Pro Ser Asp Ile Ala Val Glu Trp Glu Ser Ser Gly Gln
```

```
                35                  40                  45
Pro Glu Asn Asn Tyr Asn Thr Thr Pro Pro Met Leu Asp Ser Asp Gly
        50                  55                  60

Ser Phe Phe Leu Tyr Ser Lys Leu Thr Val Asp Lys Ser Arg Trp Gln
 65                  70                  75                  80

Gln Gly Asn Ile Phe Ser Cys Ser Val Met His Glu Ala Leu His Asn
                85                  90                  95

Arg Phe Thr Gln Lys Ser Leu Ser Leu Ser Pro Gly Lys
            100                 105

<210> SEQ ID NO 5
<211> LENGTH: 109
<212> TYPE: PRT
<213> ORGANISM: Homo sapiens

<400> SEQUENCE: 5

Ala Lys Gly Gln Pro Arg Glu Pro Gln Val Tyr Thr Leu Pro Pro Ser
 1               5                  10                  15

Gln Glu Glu Met Thr Lys Asn Gln Val Ser Leu Thr Cys Leu Val Lys
                20                  25                  30

Gly Phe Tyr Pro Ser Asp Ile Ala Val Glu Trp Glu Ser Asn Gly Gln
            35                  40                  45

Pro Glu Asn Asn Tyr Lys Thr Thr Pro Pro Val Leu Asp Ser Asp Gly
        50                  55                  60

Ser Phe Phe Leu Tyr Ser Arg Leu Thr Val Asp Lys Ser Arg Trp Gln
 65                  70                  75                  80

Glu Gly Asn Val Phe Ser Cys Ser Val Met His Glu Ala Leu His Asn
                85                  90                  95

His Tyr Thr Gln Lys Ser Leu Ser Leu Ser Leu Gly Lys
            100                 105

<210> SEQ ID NO 6
<211> LENGTH: 109
<212> TYPE: PRT
<213> ORGANISM: Artificial Sequence
<220> FEATURE:
<223> OTHER INFORMATION: Human IgG1 CH3 region - S364A

<400> SEQUENCE: 6

Ala Lys Gly Gln Pro Arg Glu Pro Gln Val Tyr Thr Leu Pro Pro Ser
 1               5                  10                  15

Arg Glu Glu Met Thr Lys Asn Gln Val Ala Leu Thr Cys Leu Val Lys
                20                  25                  30

Gly Phe Tyr Pro Ser Asp Ile Ala Val Glu Trp Glu Ser Asn Gly Gln
            35                  40                  45

Pro Glu Asn Asn Tyr Lys Thr Thr Pro Pro Val Leu Asp Ser Asp Gly
        50                  55                  60

Ser Phe Phe Leu Tyr Ser Lys Leu Thr Val Asp Lys Ser Arg Trp Gln
 65                  70                  75                  80

Gln Gly Asn Val Phe Ser Cys Ser Val Met His Glu Ala Leu His Asn
                85                  90                  95

His Tyr Thr Gln Lys Ser Leu Ser Leu Ser Pro Gly Lys
            100                 105

<210> SEQ ID NO 7
<211> LENGTH: 109
<212> TYPE: PRT
<213> ORGANISM: Artificial sequence
```

<220> FEATURE:
<223> OTHER INFORMATION: Human IgG2 CH3 region - S364A

<400> SEQUENCE: 7

Thr Lys Gly Gln Pro Arg Glu Pro Gln Val Tyr Thr Leu Pro Pro Ser
1               5                   10                  15

Arg Glu Glu Met Thr Lys Asn Gln Val Ala Leu Thr Cys Leu Val Lys
            20                  25                  30

Gly Phe Tyr Pro Ser Asp Ile Ala Val Glu Trp Glu Ser Asn Gly Gln
        35                  40                  45

Pro Glu Asn Asn Tyr Lys Thr Thr Pro Pro Met Leu Asp Ser Asp Gly
    50                  55                  60

Ser Phe Phe Leu Tyr Ser Lys Leu Thr Val Asp Lys Ser Arg Trp Gln
65                  70                  75                  80

Gln Gly Asn Val Phe Ser Cys Ser Val Met His Glu Ala Leu His Asn
                85                  90                  95

His Tyr Thr Gln Lys Ser Leu Ser Leu Ser Pro Gly Lys
            100                 105

<210> SEQ ID NO 8
<211> LENGTH: 109
<212> TYPE: PRT
<213> ORGANISM: Artificial Sequence
<220> FEATURE:
<223> OTHER INFORMATION: Human IgG3 CH3 region - S364A

<400> SEQUENCE: 8

Thr Lys Gly Gln Pro Arg Glu Pro Gln Val Tyr Thr Leu Pro Pro Ser
1               5                   10                  15

Arg Glu Glu Met Thr Lys Asn Gln Val Ala Leu Thr Cys Leu Val Lys
            20                  25                  30

Gly Phe Tyr Pro Ser Asp Ile Ala Val Glu Trp Glu Ser Ser Gly Gln
        35                  40                  45

Pro Glu Asn Asn Tyr Asn Thr Thr Pro Pro Met Leu Asp Ser Asp Gly
    50                  55                  60

Ser Phe Phe Leu Tyr Ser Lys Leu Thr Val Asp Lys Ser Arg Trp Gln
65                  70                  75                  80

Gln Gly Asn Ile Phe Ser Cys Ser Val Met His Glu Ala Leu His Asn
                85                  90                  95

Arg Phe Thr Gln Lys Ser Leu Ser Leu Ser Pro Gly Lys
            100                 105

<210> SEQ ID NO 9
<211> LENGTH: 109
<212> TYPE: PRT
<213> ORGANISM: Artificial sequence
<220> FEATURE:
<223> OTHER INFORMATION: Human IgG4 CH3 region - S364A

<400> SEQUENCE: 9

Ala Lys Gly Gln Pro Arg Glu Pro Gln Val Tyr Thr Leu Pro Pro Ser
1               5                   10                  15

Gln Glu Glu Met Thr Lys Asn Gln Val Ala Leu Thr Cys Leu Val Lys
            20                  25                  30

Gly Phe Tyr Pro Ser Asp Ile Ala Val Glu Trp Glu Ser Asn Gly Gln
        35                  40                  45

Pro Glu Asn Asn Tyr Lys Thr Thr Pro Pro Val Leu Asp Ser Asp Gly
    50                  55                  60

```
Ser Phe Phe Leu Tyr Ser Arg Leu Thr Val Asp Lys Ser Arg Trp Gln
 65                  70                  75                  80

Glu Gly Asn Val Phe Ser Cys Ser Val Met His Glu Ala Leu His Asn
             85                  90                  95

His Tyr Thr Gln Lys Ser Leu Ser Leu Ser Leu Gly Lys
            100                 105

<210> SEQ ID NO 10
<211> LENGTH: 109
<212> TYPE: PRT
<213> ORGANISM: Artificial sequence
<220> FEATURE:
<223> OTHER INFORMATION: Human IgG1 CH3 region - S364V

<400> SEQUENCE: 10

Ala Lys Gly Gln Pro Arg Glu Pro Gln Val Tyr Thr Leu Pro Pro Ser
 1               5                  10                  15

Arg Glu Glu Met Thr Lys Asn Gln Val Val Leu Thr Cys Leu Val Lys
             20                  25                  30

Gly Phe Tyr Pro Ser Asp Ile Ala Val Glu Trp Glu Ser Asn Gly Gln
         35                  40                  45

Pro Glu Asn Asn Tyr Lys Thr Thr Pro Pro Val Leu Asp Ser Asp Gly
 50                  55                  60

Ser Phe Phe Leu Tyr Ser Lys Leu Thr Val Asp Lys Ser Arg Trp Gln
 65                  70                  75                  80

Gln Gly Asn Val Phe Ser Cys Ser Val Met His Glu Ala Leu His Asn
             85                  90                  95

His Tyr Thr Gln Lys Ser Leu Ser Leu Ser Pro Gly Lys
            100                 105

<210> SEQ ID NO 11
<211> LENGTH: 109
<212> TYPE: PRT
<213> ORGANISM: Artificial sequence
<220> FEATURE:
<223> OTHER INFORMATION: Human IgG2 CH3 region - S364V

<400> SEQUENCE: 11

Thr Lys Gly Gln Pro Arg Glu Pro Gln Val Tyr Thr Leu Pro Pro Ser
 1               5                  10                  15

Arg Glu Glu Met Thr Lys Asn Gln Val Val Leu Thr Cys Leu Val Lys
             20                  25                  30

Gly Phe Tyr Pro Ser Asp Ile Ala Val Glu Trp Glu Ser Asn Gly Gln
         35                  40                  45

Pro Glu Asn Asn Tyr Lys Thr Thr Pro Pro Met Leu Asp Ser Asp Gly
 50                  55                  60

Ser Phe Phe Leu Tyr Ser Lys Leu Thr Val Asp Lys Ser Arg Trp Gln
 65                  70                  75                  80

Gln Gly Asn Val Phe Ser Cys Ser Val Met His Glu Ala Leu His Asn
             85                  90                  95

His Tyr Thr Gln Lys Ser Leu Ser Leu Ser Pro Gly Lys
            100                 105

<210> SEQ ID NO 12
<211> LENGTH: 109
<212> TYPE: PRT
<213> ORGANISM: Artificial sequence
<220> FEATURE:
<223> OTHER INFORMATION: Human IgG3 CH3 region - S364V
```

```
<400> SEQUENCE: 12

Thr Lys Gly Gln Pro Arg Glu Pro Gln Val Tyr Thr Leu Pro Pro Ser
1               5                   10                  15

Arg Glu Glu Met Thr Lys Asn Gln Val Val Leu Thr Cys Leu Val Lys
                20                  25                  30

Gly Phe Tyr Pro Ser Asp Ile Ala Val Glu Trp Glu Ser Ser Gly Gln
            35                  40                  45

Pro Glu Asn Asn Tyr Asn Thr Thr Pro Pro Met Leu Asp Ser Asp Gly
        50                  55                  60

Ser Phe Phe Leu Tyr Ser Lys Leu Thr Val Asp Lys Ser Arg Trp Gln
65                  70                  75                  80

Gln Gly Asn Ile Phe Ser Cys Ser Val Met His Glu Ala Leu His Asn
                85                  90                  95

Arg Phe Thr Gln Lys Ser Leu Ser Leu Ser Pro Gly Lys
                100                 105

<210> SEQ ID NO 13
<211> LENGTH: 109
<212> TYPE: PRT
<213> ORGANISM: Artificial sequence
<220> FEATURE:
<223> OTHER INFORMATION: Human IgG4 CH3 region - S364V

<400> SEQUENCE: 13

Ala Lys Gly Gln Pro Arg Glu Pro Gln Val Tyr Thr Leu Pro Pro Ser
1               5                   10                  15

Gln Glu Glu Met Thr Lys Asn Gln Val Val Leu Thr Cys Leu Val Lys
                20                  25                  30

Gly Phe Tyr Pro Ser Asp Ile Ala Val Glu Trp Glu Ser Asn Gly Gln
            35                  40                  45

Pro Glu Asn Asn Tyr Lys Thr Thr Pro Pro Val Leu Asp Ser Asp Gly
        50                  55                  60

Ser Phe Phe Leu Tyr Ser Arg Leu Thr Val Asp Lys Ser Arg Trp Gln
65                  70                  75                  80

Glu Gly Asn Val Phe Ser Cys Ser Val Met His Glu Ala Leu His Asn
                85                  90                  95

His Tyr Thr Gln Lys Ser Leu Ser Leu Ser Leu Gly Lys
                100                 105
```